United States Patent
Gallardo et al.

(10) Patent No.: US 10,743,932 B2
(45) Date of Patent: *Aug. 18, 2020

(54) INTEGRATED ABLATION SYSTEM USING CATHETER WITH MULTIPLE IRRIGATION LUMENS

(75) Inventors: Diana Gallardo, Perris, CA (US); Assaf Govari, Haifa (IL); Jeffrey W. Schultz, Chino, CA (US); Michael Olen Zirkle, Yorba Linda, CA (US)

(73) Assignee: Biosense Webster (Israel) Ltd., Yokneam (IL)

(*) Notice: Subject to any disclaimer, the term of this patent is extended or adjusted under 35 U.S.C. 154(b) by 1087 days.

This patent is subject to a terminal disclaimer.

(21) Appl. No.: 13/193,277

(22) Filed: Jul. 28, 2011

(65) Prior Publication Data

US 2013/0030426 A1    Jan. 31, 2013

(51) Int. Cl.
*A61B 18/14*    (2006.01)
*A61B 18/00*    (2006.01)
(Continued)

(52) U.S. Cl.
CPC .... *A61B 18/1492* (2013.01); *A61B 2017/003* (2013.01); *A61B 2018/00577* (2013.01);
(Continued)

(58) Field of Classification Search
CPC ............... A61B 18/1492; A61B 18/02; A61B 2018/00214; A61B 2218/002
(Continued)

(56) References Cited

U.S. PATENT DOCUMENTS 4,552,127 A * 11/1985 Schiff ............... A61B 5/042
                                               600/18
5,458,630 A * 10/1995 Hoegnelid ........... A61N 1/05
                                               607/116
(Continued)

FOREIGN PATENT DOCUMENTS

CN       101856271 A    10/2010
EP       1 498 080 A1    1/2005
(Continued)

OTHER PUBLICATIONS

European Patent Office Extended European Search Report for EP 12178150.4, dated Nov. 5, 2012, 8 pgs.
(Continued)

*Primary Examiner* — Ronald Hupczey, Jr.
*Assistant Examiner* — Yasamin Ekrami
(74) *Attorney, Agent, or Firm* — Lewis Roca Rothgerber Christie LLP

(57) ABSTRACT

A catheter adapted for ablation has multiple dedicated irrigation tubings to supply fluid to their respective electrode or set of electrodes. The tubings provide parallel flow pathways through the catheter where irrigation fluid is delivered to irrigated tip and/or ring electrodes which can accomplish uni-polar or bi-polar ablation. Such separate and dedicated fluid pathways allow fluid to be delivered to the corresponding electrode or set of electrodes at different flow rates. An integrated ablation system using such catheter has an ablation energy source and an irrigation pump with multiple pump heads that can operate independently of each other. An integrated irrigation tubing set is included to extend between the fluid source and the catheter, with each pump head being able to act on a different tubing that delivers fluid to a different electrode or set of electrodes.

9 Claims, 11 Drawing Sheets

(51) Int. Cl.
*A61B 17/00* (2006.01)
*A61B 34/20* (2016.01)

(52) U.S. Cl.
CPC ............... *A61B 2018/00821* (2013.01); *A61B 2034/2051* (2016.02); *A61B 2217/007* (2013.01); *A61B 2218/002* (2013.01)

(58) Field of Classification Search
USPC ........................................................ 606/41
See application file for complete search history.

(56) References Cited

U.S. PATENT DOCUMENTS

| | | | |
|---|---|---|---|
| 5,964,757 | A | 10/1999 | Ponzi |
| 5,989,240 | A | 11/1999 | Strowe |
| 6,217,574 | B1 | 4/2001 | Webster |
| 6,302,880 | B1 | 10/2001 | Schaer |
| 6,371,955 | B1 | 4/2002 | Fuimaono et al. |
| 6,394,983 | B1 | 5/2002 | Mayoral et al. |
| 6,400,976 | B1 | 6/2002 | Champeau |
| 6,468,260 | B1 | 10/2002 | Bumbalough et al. |
| 6,500,167 | B1 | 12/2002 | Webster, Jr. |
| 6,522,930 | B1 | 2/2003 | Schaer et al. |
| 6,522,933 | B2 | 2/2003 | Nguyen |
| 6,666,864 | B2 | 12/2003 | Bencini et al. |
| 6,706,039 | B2* | 3/2004 | Mulier ............... A61B 18/14 606/41 |
| 6,723,094 | B1 | 4/2004 | Desinger |
| 6,855,143 | B2 | 2/2005 | Davison et al. |
| 6,887,237 | B2 | 5/2005 | McGaffigan |
| 7,156,845 | B2 | 1/2007 | Mulier et al. |
| 7,306,593 | B2* | 12/2007 | Keidar et al. ............. 606/34 |
| 7,416,552 | B2 | 8/2008 | Paul et al. |
| 7,615,049 | B2 | 11/2009 | West et al. |
| 8,617,087 | B2 | 12/2013 | Schultz |
| 8,764,742 | B2* | 7/2014 | Pappone ........... A61M 25/003 606/41 |
| 2001/0025178 | A1* | 9/2001 | Mulier ............... A61B 18/14 606/41 |
| 2002/0111618 | A1 | 8/2002 | Stewart et al. |
| 2005/0234446 | A1* | 10/2005 | Van Wyk et al. ............. 606/41 |
| 2006/0025751 | A1 | 2/2006 | Roy et al. |
| 2006/0106298 | A1 | 5/2006 | Ahmed et al. |
| 2006/0184106 | A1* | 8/2006 | McDaniel .......... A61B 18/1492 604/95.04 |
| 2006/0241366 | A1* | 10/2006 | Falwell et al. ................ 600/374 |
| 2007/0156114 | A1 | 7/2007 | Worley et al. |
| 2008/0161795 | A1 | 7/2008 | Wang et al. |
| 2009/0093811 | A1 | 4/2009 | Koblish et al. |
| 2009/0125016 | A1 | 5/2009 | Wang et al. |
| 2009/0163912 | A1 | 6/2009 | Wang et al. |
| 2009/0216284 | A1 | 8/2009 | Chin et al. |
| 2009/0254083 | A1 | 10/2009 | Wallace et al. |
| 2010/0004632 | A1 | 1/2010 | Wu et al. |
| 2010/0057074 | A1* | 3/2010 | Roman ............... A61B 18/1492 606/33 |
| 2010/0063478 | A1 | 3/2010 | Selkee |
| 2010/0121138 | A1 | 5/2010 | Goldenberg et al. |
| 2010/0168548 | A1 | 7/2010 | Govari et al. |
| 2010/0222859 | A1* | 9/2010 | Govari ................ A61B 5/0422 607/119 |
| 2010/0286590 | A1* | 11/2010 | Durand ............... A61K 9/0009 604/20 |
| 2011/0160721 | A1* | 6/2011 | Wang ................. A61B 18/1492 606/41 |
| 2012/0116387 | A1* | 5/2012 | Govari et al. ................. 606/41 |
| 2012/0143088 | A1 | 6/2012 | Schultz |
| 2012/0172703 | A1 | 7/2012 | Esguerra et al. |
| 2012/0271145 | A1* | 10/2012 | Govari et al. ................ 600/409 |
| 2013/0006238 | A1 | 1/2013 | Ditter et al. |

FOREIGN PATENT DOCUMENTS

| | | |
|---|---|---|
| EP | 2 335 632 A2 | 6/2011 |
| WO | WO 96/05768 A1 | 2/1996 |
| WO | WO 99/56812 | 11/1999 |
| WO | WO 2006/003216 A1 | 1/2006 |

OTHER PUBLICATIONS

Extended European Search Report dated Oct. 2, 2013 in EP application No. 13178078.5, 4 pages.

EP Office action dated Dec. 8, 2014 in EP application No. 12178150.4, 6 pages.

SIPO P.R. China First Office Action dated Aug. 4, 2015 for Chinese Patent Application No. 201210265424.1, 3 pages (English translation only).

Extended European Search Report and Office action dated Feb. 10, 2016 in EP application No. 15194767.8, 10 pages.

* cited by examiner

| CONDITION | TIP ELECTRODE FLOW RATE (mL/min) | RING ELECTRODE FLOW RATE (mL/min) | TOTAL FLOW RATE (mL/min)* |
|---|---|---|---|
| Maintenance Flow | 2 | 2 | 8 |
| Focal Ablation from Tip Electrode | 15 | 2 | 21 |
| Linear Ablation from All Tip and Ring Electrodes | 15 | 6 | 33 |

* value based on 3 ring electrodes

FIG. 11

INTEGRATED ABLATION SYSTEM USING CATHETER WITH MULTIPLE IRRIGATION LUMENS

FIELD OF INVENTION

This invention relates generally to methods and devices for invasive medical treatment, and specifically to catheters, in particular, irrigated ablation catheters.

BACKGROUND

Ablation of myocardial tissue is well known as a treatment for cardiac arrhythmias. In radio-frequency (RF) ablation, for example a catheter is inserted into the heart and brought into contact with tissue at a target location. RF energy is then applied through electrodes on the catheter in order to create a lesion for the purpose of breaking arrhythmogenic current paths in the tissue.

Ablation has been accomplished primarily by means of focal ablation, that is, ablation by a tip electrode at a distal end of the catheter. Thus, for linear ablation along a line or curve, the tip electrode is repositioned repeatedly or dragged across the tissue along the line or curve during a prolonged ablation.

Also known are irrigated ablation tip and ring electrodes which are effective at reducing electrode temperature during ablation to minimize the formation of char and coagulum. However, fluid load on the patient is a concern, especially where multiple electrodes are being irrigated.

Current EP catheters utilize a single irrigation lumen to deliver irrigation to one or more irrigated electrodes. Pump units consisting of one pump head are therefore used. As catheters become more complex, the need for multiple irrigation lumens becomes more critical. Currently, irrigation delivery to a catheter with multiple irrigation lumens requires the use of multiple pump units.

Accordingly, there is a desire for a catheter adapted for both focal and linear ablation so that a linear lesion can be formed without repositioning of the catheter. In particular, there is a desire for a catheter with tip and ring electrodes adapted for uni-polar and bi-polar ablation. Such a catheter would advantageously reduce procedure time and improve clinical efficacy of such procedures. And where such tip and ring electrodes are irrigated, there is also a desire that the fluid flow through these electrodes be controlled and variable, if not also dependent on the selective energization of the irrigated electrodes. To that end, there is a further desire for an integrated ablation system that includes an irrigation pump adapted to supply fluid in multiple independent flow paths so that selected electrodes or sets of electrodes can receive fluid at different flow rates, especially where the flow rates are dependent on the energization state of the electrodes.

SUMMARY OF THE INVENTION

The present invention includes a catheter adapted for ablation with multiple irrigation tubings, each being dedicated to supplying irrigation fluid to a selected electrode or set of electrodes. The tubings provide a generally parallel flow paths through the catheter where irrigation fluid is delivered to irrigation ablation electrodes via pathways that are separate and isolated from each other so that fluid can be delivered at different flow rates to different electrodes. For example, an operator may wish to deliver fluid at a higher flow rate to ablating electrodes for cooling and to deliver fluid at a lower flow rate to nonablating electrodes to minimize fluid load on the patient while flushing the electrode irrigation apertures.

In one embodiment, the catheter includes an elongated body, a deflectable intermediate section, and a distal section with at least two electrodes. The catheter further includes a first irrigation tubing and a second irrigation tubing, wherein each irrigation tubing defines an independent and dedicated irrigation flow pathway to a respective electrode, which allows each electrode to receive (and thus emit) fluid at a different flow rate.

In a more detailed embodiment, the catheter carries either an irrigated tip electrode in combination with a plurality of irrigated ring electrodes, or only a plurality of irrigated ring electrodes. In the former instance, one irrigation tubing delivers fluid, such as saline, to the distally mounted tip electrode while the other irrigation tubing delivers fluid to one or more of the ring electrodes. This embodiment may be particularly useful where all electrodes may be utilized to perform linear bi-polar or uni-polar ablations using RF power, as well as focal uni-polar ablations from only the tip electrode. The ability to provide fluid to the ring electrodes, tip electrodes, or combination of electrodes limits patient loading of fluid (such as saline) when electrodes are not utilized. Furthermore, differences in tip and ring electrode designs may require differing irrigation flow rates to achieve similar clinical outcomes under similar RF deliver conditions.

In the other embodiment where the catheter carries only irrigated ring electrodes, linear type lesions are formed using either uni-polar or bi-polar RF ablation. One irrigation tubing delivers fluid to one subset of ring electrodes while the second irrigation tubing delivers fluid to the remaining subset of electrodes. Utilization of two or more irrigation lumens to deliver fluid to at least two subsets of electrodes provide several benefits, including (i) irrigation fluid may be delivered only to those electrodes requiring irrigation, thereby limiting fluid loading to the patient; and (ii) multiple irrigation lumens provide more uniform fluid delivery of irrigation fluid from each electrode as the effect of reducing driving pressure and mass flow rate is minimized across the electrodes.

The present invention is also directed to an integrated ablation system having a catheter with at least two electrodes, an ablation energy source and an irrigation pump with at least two pump heads, each adapted to operate independently. The system also includes at least one fluid source and an integrated irrigation tubing set providing at least a first fluid pathway between the at least one fluid source and one electrode and at least a second fluid pathway between the at least one fluid source and the other electrode. The system advantageously allows the electrodes to be selectively energized by the ablation energy source, whereupon the irrigation pump is adapted to operate each pump head in accordance with energization state of the respective electrode. For example, the pump head of one electrode may operate to provide fluid at one flow rate when that electrode is energized and the pump head of another electrode may operate to provide fluid at another flow rate when that electrode is energized. Moreover, each pump head may operate at yet another flow rate when the corresponding electrode is not utilized (or de-energized, used interchangeably herein).

Accordingly, the irrigation pump with multiple pump heads provides independent control of irrigation to the multiple irrigation lumens of the catheter. Subject to the control of the RF generator, each pump head is controlled independently to supply fluid to its respective electrode or set of electrodes. To that end, an integrated irrigation tubing set with multiple parallel tubings extends between the fluid source(s) and the catheter, thus simplifying the use of tubings and reducing the number of tubings needed. The integrated irrigation tubing set provides parallel fluid paths through the irrigation pump with each pump head acting on a respective tubing to provide the desired flow rate through that tubing.

BRIEF DESCRIPTION OF THE DRAWINGS

These and other features and advantages of the present invention will be better understood by reference to the following detailed description when considered in conjunction with the accompanying drawings. It is understood that selected structures and features have not been shown in certain drawings so as to provide better viewing of the remaining structures and features.

FIG. 11 is a table showing sample fluid flow rates for various operating conditions of the system.

DETAILED DESCRIPTION OF THE INVENTION

Figure 1:
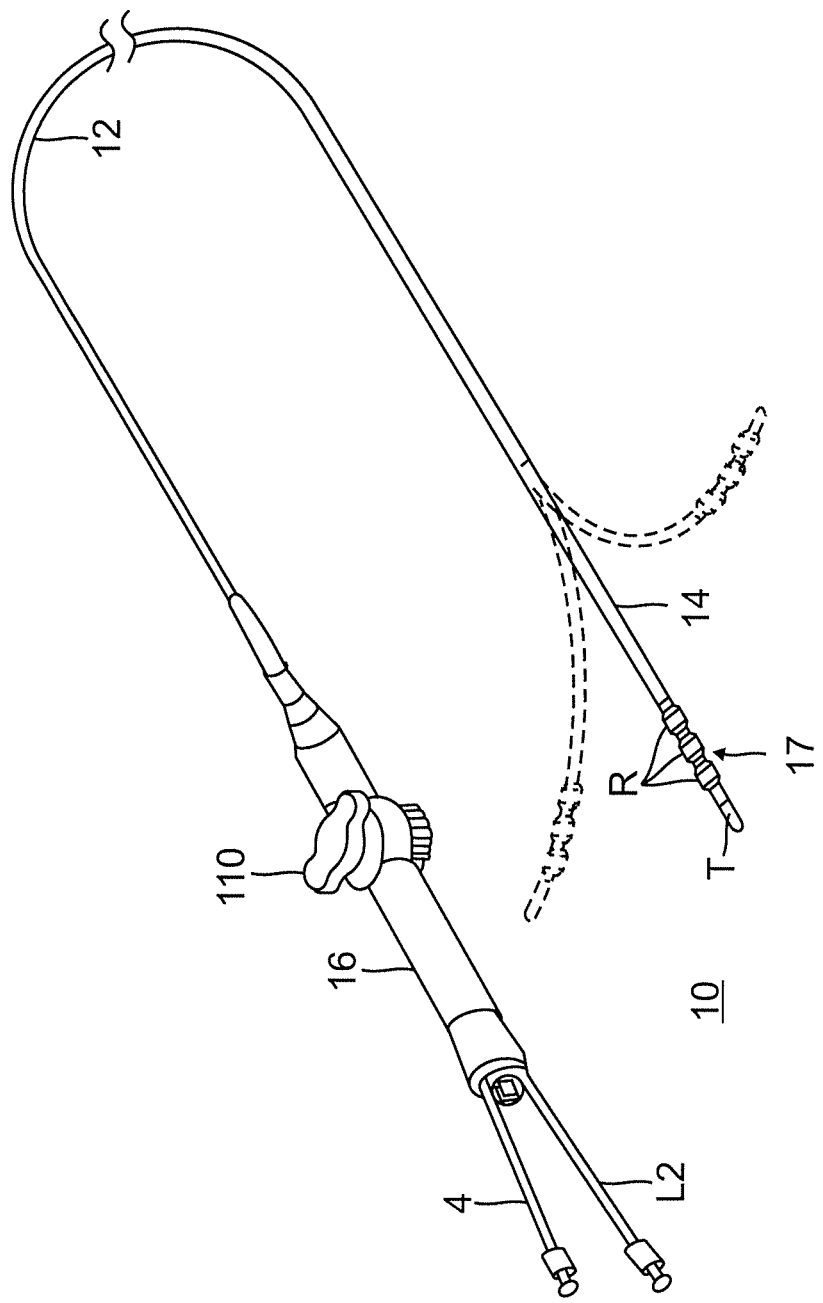
FIG. 1 is a perspective view of an embodiment of a catheter in accordance with the present invention.

As illustrated in FIG. 1, the present invention includes a steerable catheter 10 with multiple electrodes, including a tip electrode T and a plurality of ring electrodes R, with at least two flow-separated and flow-isolated irrigation lumens L1, L2 to separately and independently deliver fluid to the tip and ring electrodes. The catheter is deployed in a target region of the body, e.g., the atria of the heart, and designed to facilitate linear ablation along target tissue by means of radiofrequency (RF) current. The catheter is advantageously designed to form a generally continuous RF lesion without the need to reposition the catheter. Once placed, the catheter can remain in position whereupon RF energy is selectively delivered through the ring electrodes to form the generally continuous RF lesion. In one embodiment, RF energy is delivered through each of the ring electrodes as uni-polar electrodes to the contacting target tissue to a return electrode (e.g., an external electrode patch affixed to the patient's back) to accomplish focal uni-polar lesions. Then, to "connect" the uni-polar lesions so as to form a generally continuous linear lesion, tissue in between each of the focal lesion is ablated by energizing the ring electrodes as bi-polar electrodes to form bi-polar lesions between the ring electrodes. Accordingly, the present system allows for faster lesion formation with reduced catheter manipulation.

Figure 2:
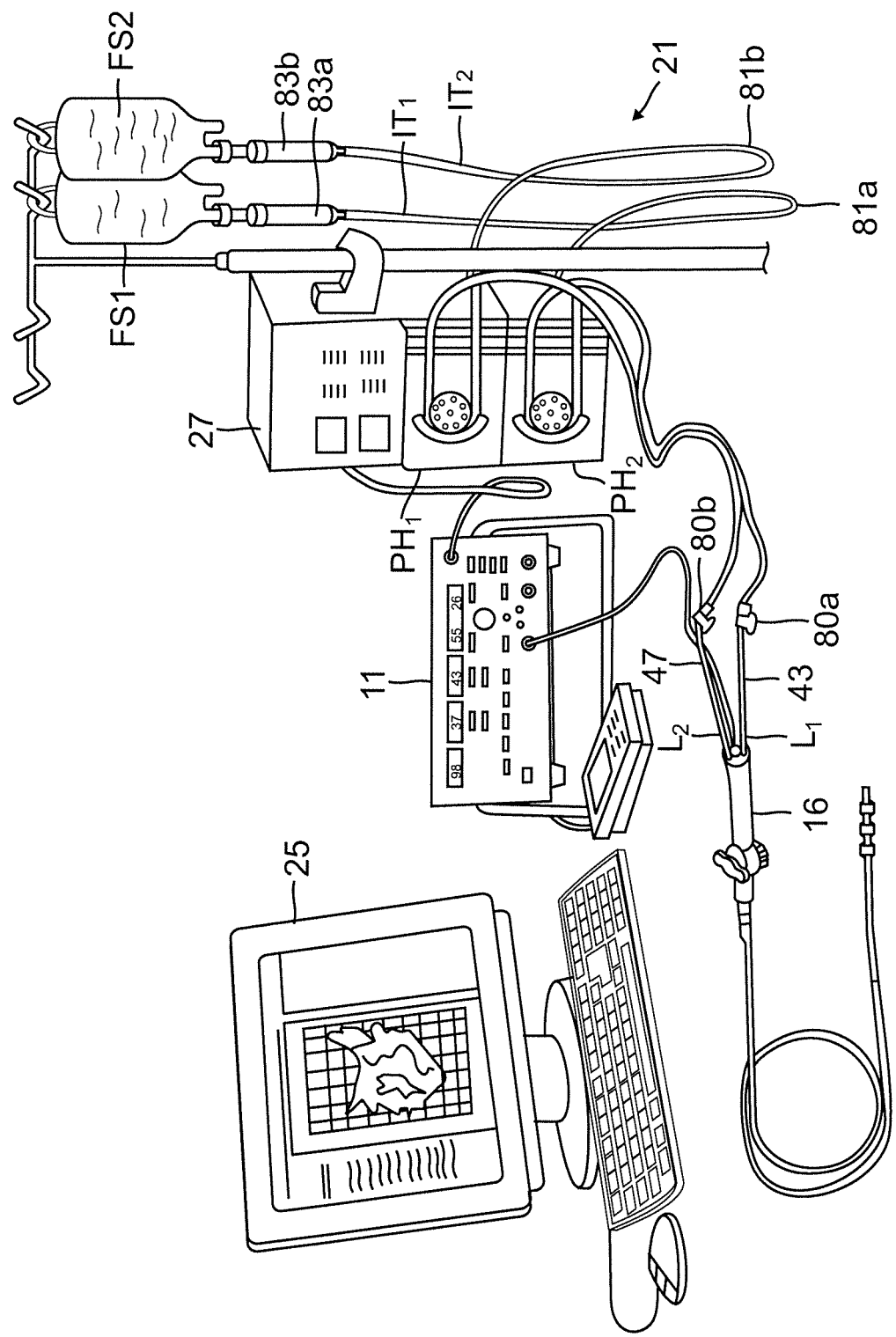
FIG. 2 is a perspective view of an embodiment of an integrated ablation system in accordance with the present invention.
Figure 3:
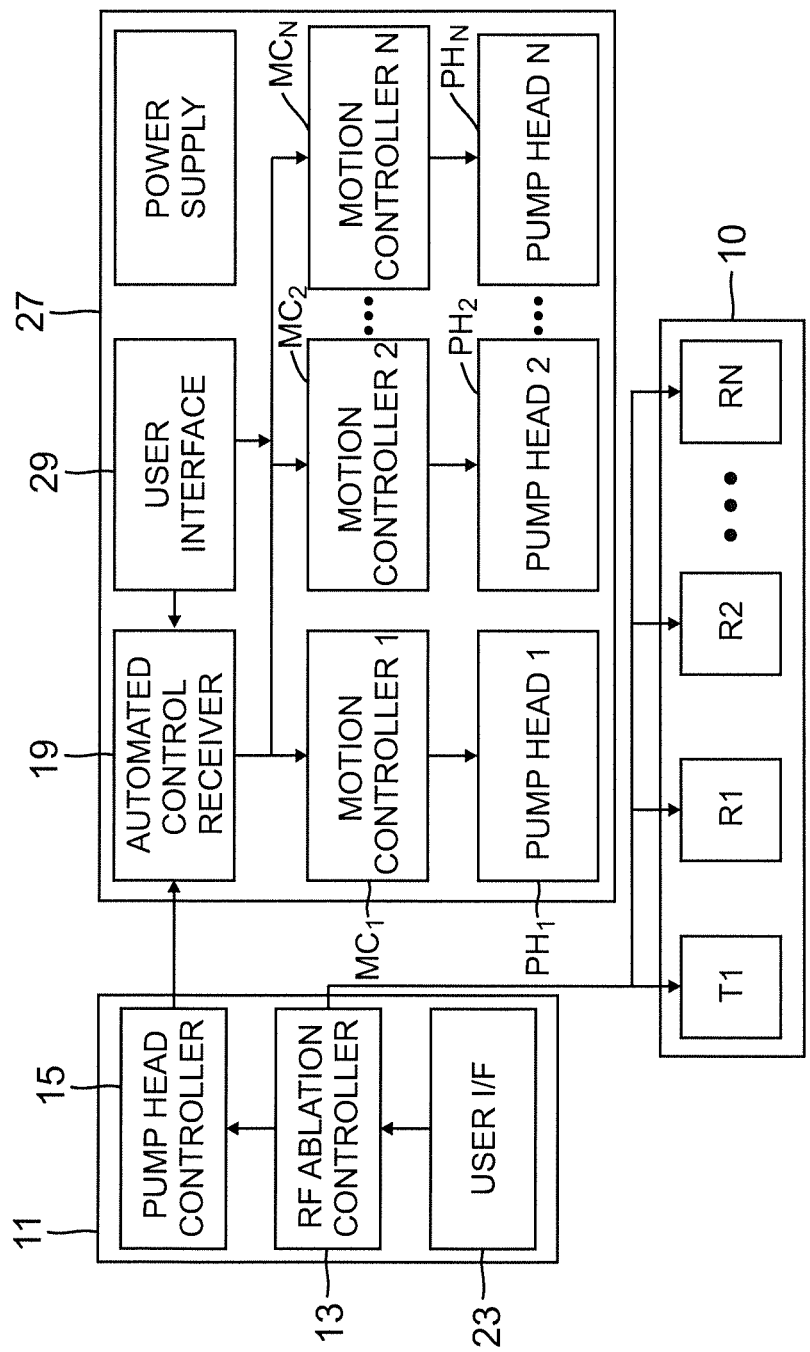
FIG. 3 is a block diagram of the system of FIG. 2.

As illustrated in FIGS. 2 and 3, the catheter 10 may be used with an integrated ablation system S which in one embodiment includes an external control system, for example, a multi-channel RF generator 11 with an RF ablation controller 13, a pump head controller 15, and a visual display 25. The system S also includes an irrigation pump 27 with an automated control receiver 19 in communication with multiple motion controllers MC1-MCN with respective pump heads PH1-PHN, e.g., at least two pump heads PH1, PH2, that deliver irrigation fluid to the catheter which is equipped with multiple irrigation lumens, each providing a dedicated flow path to one electrode or a set of electrodes to the exclusion of other electrode(s) or set(s) of electrodes.

The RF generator 11 has built in logic which allows for automated independent operation of each pump head based on ablation settings. User interface 23 on the RF generator allows the user to modify or define custom parameters for the operation of the pump heads for increased control over the process.

Ablation is delivered at a set wattage on the multi-channel RF generator 11. The irrigation pump 27 can be a peristaltic pump, or roller pump, using positive displacement for pumping fluids. As understood by one of ordinary skill in the art, a peristaltic pump has a flexible tube fitted inside a pump casing, which is typically circular, although a linear peristaltic pump may be used as well. Moreover, the irrigation pump may further include bubble sensors, occlusion sensors or any other sensor utilized for the safe operation of the pump.

The multi-channel RF generator 11 routes the RF current through selected electrodes in accordance with ablation parameters set and controlled by an operator via the user interface 23. For example, (i) all electrodes may be energized simultaneously, (ii) the tip electrode may be energized to the exclusion of all ring electrodes, and (iii) vice versa, (iv) the tip electrode may be energized in combination with selective ring electrodes, or (v) all or only selective ring electrodes may be energized. Moreover, any combination or sequence of any of these energization patterns in series is possible, all obviating the need to reposition the catheter during ablation of a linear lesion.

During ablation, the multi-channel RF generator also monitors the temperature of the electrode(s) involved and reduces the wattage if the temperature exceeds a value set by the user. Catheter temperature information is sent from a thermocouple on the catheter to the RF generator.

In accordance with the invention, the RF generator 11 also communicates with the irrigation pump 27 via the pump head controller 15 to control irrigation flow delivery in accordance with the selective energization of the electrodes for optimizing fluid flow to the catheter. That is, while RF energy is being delivered through one electrode or set of electrodes, the RF generator triggers the corresponding pump head(s) to deliver fluid at the desired flow rate(s) to that one electrode or set of electrodes. If RF energy is being applied to all electrodes, the RF generator triggers all pump heads to deliver fluid at the desired flow rate(s). Communication may be accomplished by the use of cabling, wireless communication technology, such as BLUETOOTH®, or by radio signals (e.g., transmitted at 2.4 GHz or other suitable frequency for use in a medical lab environment).

In response to ablation/energization signals generated by the RF ablation controller 13 indicating a state of energization or "Condition" of each electrode, the pump head controller 15 in communication with the RF ablation controller 13 sends appropriate signals to the automated controller receiver 19 of the irrigation pump 27 to control the motion controller MC1 for each pump head PHi. In response to the signals, each motion controller MC1 may actuate the respective pump head PHi to start or stop flow, and/or to increase or decrease the flow rate. For example, flow rate may be decreased for a pump head delivering irrigation fluid to an inactive electrode so as to minimize fluid load on the patient, and/or flow rate may be increased for a pump head delivering irrigation fluid to an electrode receiving increased power so as to diffuse blood in the surrounding area and minimize formation of char and coagulum due to increased electrode heating. As understood by one of ordinary skill in the art, a minimum flow rate through an inactive energized electrode is generally maintained in order to flush the irrigation apertures in the electrodes to minimize the risk of obstruction. The operator may also manually control the pump heads via the user interface 23, as desired.

Each pump head acts on a dedicated irrigation tubing that is connected to a fluid source. Thus, the system employs a parallel irrigation transport configuration 21, as shown in FIG. 2, using multiple parallel irrigation transport pathways that are dedicated and separate where each irrigation transport pathway includes a dedicated fluid source FSi, a dedicated irrigation tubing ITi that is acted on by a dedicated pump head PHi, and a dedicated catheter irrigation lumen Li that supplies a selected electrode or set of electrodes separately from other electrode(s) or set(s) of electrodes.

Referring to FIG. 1, the catheter 10 according to the disclosed embodiments comprises an elongated body that may include an insertion shaft or catheter body 12 having a longitudinal axis, and an intermediate section 14 distal of the catheter body that can be uni- or bi-directionally deflectable off-axis from the catheter body. Distal of the intermediate section 14 is a distal section 17 carrying a distal tip electrode T and a plurality of ring electrodes R adapted for ablation and irrigation.

Figure 4A:
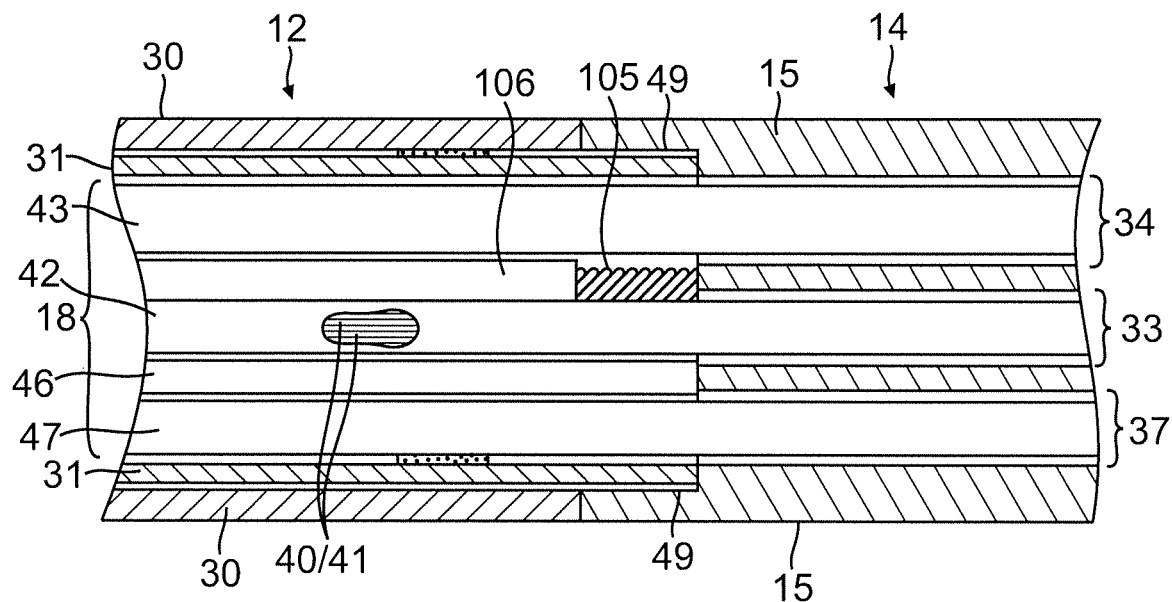
FIG. 4A is a side cross-sectional view of the catheter of FIG. 1, including a junction of a catheter body and an intermediate deflectable section, taken generally along a diameter.
Figure 4B:
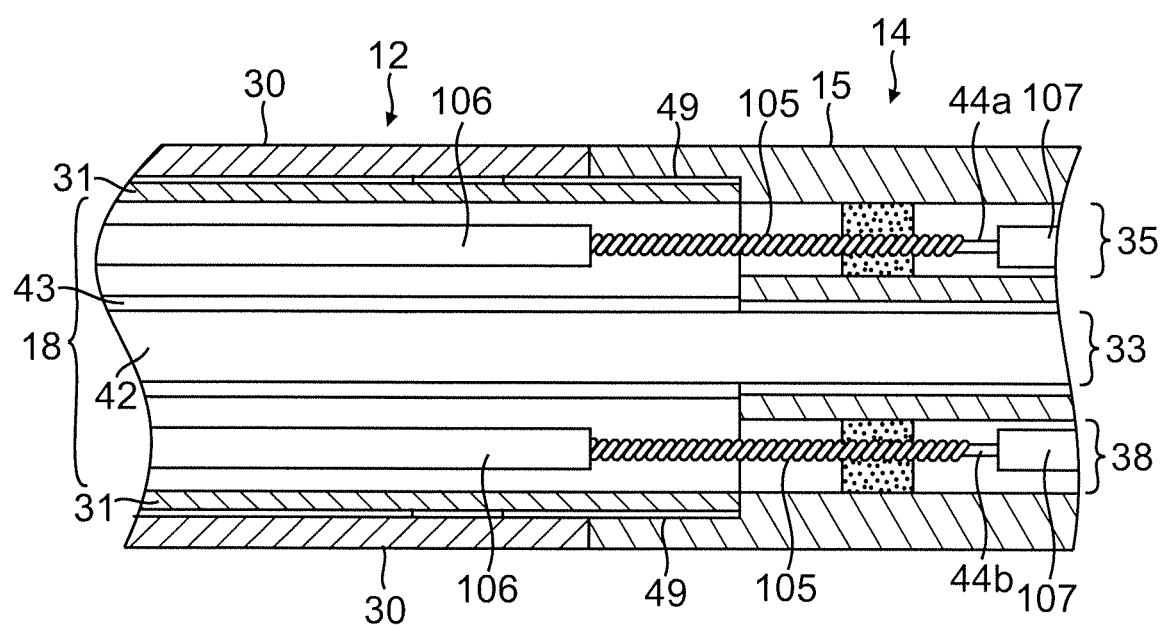
FIG. 4B is a side cross-sectional view of the catheter of FIG. 1, including a junction of a catheter body and an intermediate deflectable section, taken generally along another diameter.

In the depicted embodiment of FIGS. 4A and 4B, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A presently preferred construction comprises an outer wall 30 made of polyurethane or PEBAX. The outer wall 30 comprises an imbedded braided mesh of stainless steel or the like, as is generally known in the art, to increase torsional stiffness of the catheter body 12 so that, when the control handle 16 is rotated, the intermediate section 14 and distal section 17 will rotate in a corresponding manner.

The outer diameter of the catheter body 12 is not critical, but is preferably no more than about 8 french, more preferably 7 french. Likewise the thickness of the outer wall 30 is not critical, but is thin enough so that the central lumen 18 can accommodate any desired wires, cables and/or tubes. The inner surface of the outer wall 30 is lined with a stiffening tube 31 to provide improved torsional stability. The outer diameter of the stiffening tube 31 is about the same as or slightly smaller than the inner diameter of the outer wall 30. The stiffening tube 31 can be made of any suitable material, such as polyimide, which provides very good stiffness and does not soften at body temperature.

Figure 4C:
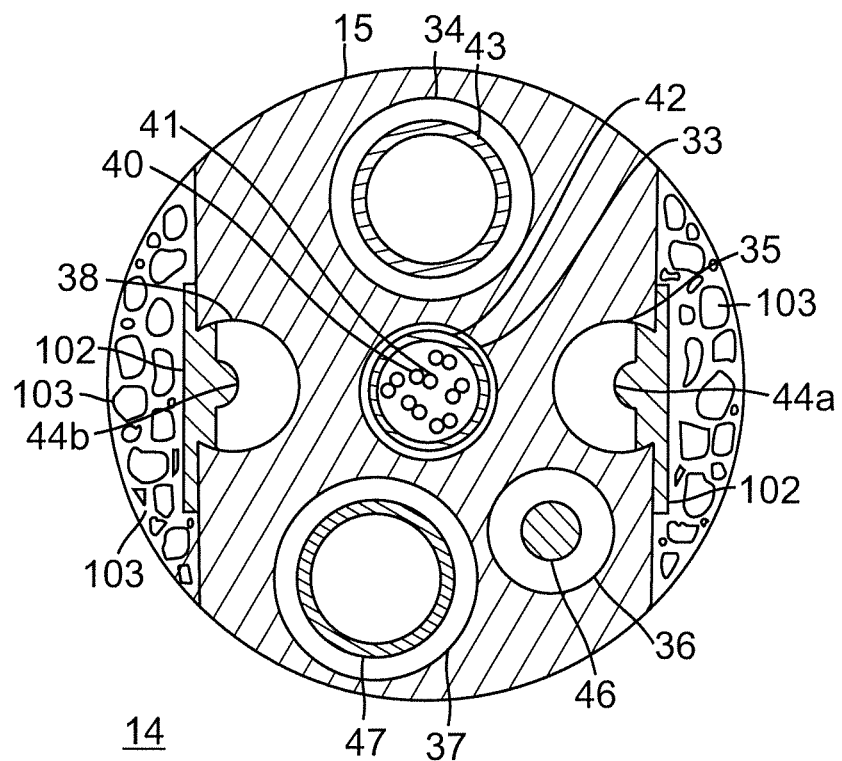
FIG. 4C is an end cross-sectional view of the catheter of FIG. 1, taking along line C-C

The deflectable intermediate section 14 comprises a short section of tubing 15 having multiple lumens, each occupied by the various components extending through the intermediate section. In the illustrated embodiment, there are six lumens as best seen in FIG. 4C. Lead wire/thermocouple pairs 40, 41 for each electrode pass through a first lumen 33 which is on-axis in the illustrated embodiment. A nonconductive protective sheath 42 is provided. A first irrigation tubing 43 for delivering fluid to an electrode or a first set of electrodes passes through a second lumen 34 which is off-axis in the illustrated embodiment. For at least unidirectional deflection, a first puller wire 44a passes through a third, off-axis lumen 35. A cable 46 for a position sensor assembly, including a plurality of single axis sensors (SAS) positioned on the distal section 17, passes through a fourth lumen 36 which is off-axis in the illustrated embodiment. A second irrigation tubing 47 for delivering fluid to another electrode or a second set of electrodes passes through a fifth lumen 37 which is off-axis in the illustrated embodiment. For bi-directional deflection, a second puller wire 44 passes through a sixth, off-axis lumen 38.

The multi-lumened tubing 15 of the intermediate section 14 is made of a suitable non-toxic material that is preferably more flexible than the catheter body 12. A suitable material is braided polyurethane or PEBAX, i.e., polyurethane or PEBAX with an embedded mesh of braided stainless steel or the like. The plurality and size of each lumen are not critical, provided there is sufficient room to house the components extending therethrough. Position of each lumen is also not critical, except the positions of the lumens 35, 38 for the puller wires 44a, 44b. The lumens 35, 38 should be off-axis, and diametrically opposite of each other for bi-directional deflection along a plane.

The useful length of the catheter, i.e., that portion that can be inserted into the body can vary as desired. Preferably the useful length ranges from about 110 cm to about 120 cm. The length of the intermediate section 14 is a relatively small portion of the useful length, and preferably ranges from about 3.5 cm to about 10 cm, more preferably from about 5 cm to about 6.5 cm.

A preferred means for attaching the catheter body 12 to the intermediate section 14 is illustrated in FIGS. 4A and 4B. The proximal end of the intermediate section 14 comprises an inner circumferential notch that receives the outer surface of the distal end of the stiffening tube 31 of the catheter body 12. The intermediate section 14 and catheter body 12 are attached by glue or the like, for example, polyurethane. If desired, a spacer (not shown) can be provided within the catheter body 12 between the distal end of the stiffening tube 31 and the proximal end of the intermediate section 14 to provide a transition in flexibility at the junction of the catheter body 12 and the intermediate section, which allows the junction to bend smoothly without folding or kinking. An example of such a spacer is described in more detail in U.S. Pat. No. 5,964,757, the disclosure of which is incorporated herein by reference.

Figure 5:
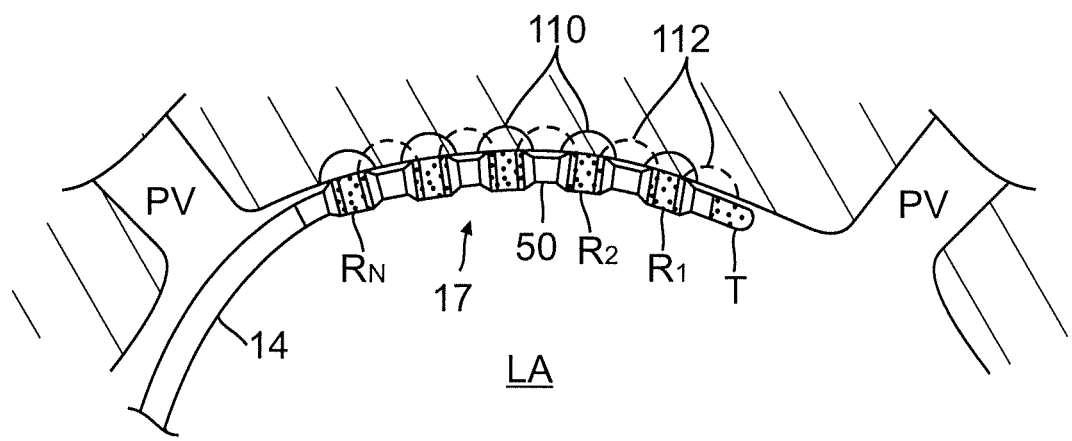
FIG. 5 is a side elevational view of an embodiment of a distal section of the catheter of FIG. 1, in contact with tissue to form lesions through ablation.

With reference to FIG. 5, distal the intermediate section 14 is the distal section 17 which includes a multi-lumened tubing 50 on which are mounted distal tip electrode T and plurality of ring electrodes R1-RN, for example, ranging between about three to nine ring electrodes. In the disclosed embodiment, there are five ring electrodes. The tubing 50 can be made of any biocompatible plastic such as polyurethane or PEBAX. In the illustrated embodiment of FIGS. 6A, 6B and 6C, the tubing 50 has four lumens 51, 52, 58 and 59. The lead wire/thermocouple pair 40, 41 for the tip electrode passes through a first, on-axis lumen 51 which is generally in axial alignment with the first lumen 33 of the intermediate section 14. A second, off-axis lumen 52 generally in axial alignment with the second lumen 34 of the intermediate section receives a distal end of the first irrigation tubing 43. The lumen 52 is sized to form a fluid-tight seal with the distal end of the tubing 43 so that fluid flows distally directly into the lumen 52. As shown in FIG. 6C, a radial opening 55 is formed in the side wall of the tubing 50 underneath each ring electrode R so that fluid flows from the lumen 52 into the ring electrodes R1-RN as shown by arrows 57. A suitable irrigation ring electrode is illustrated in detail in FIG. 7.

Figure 6A:
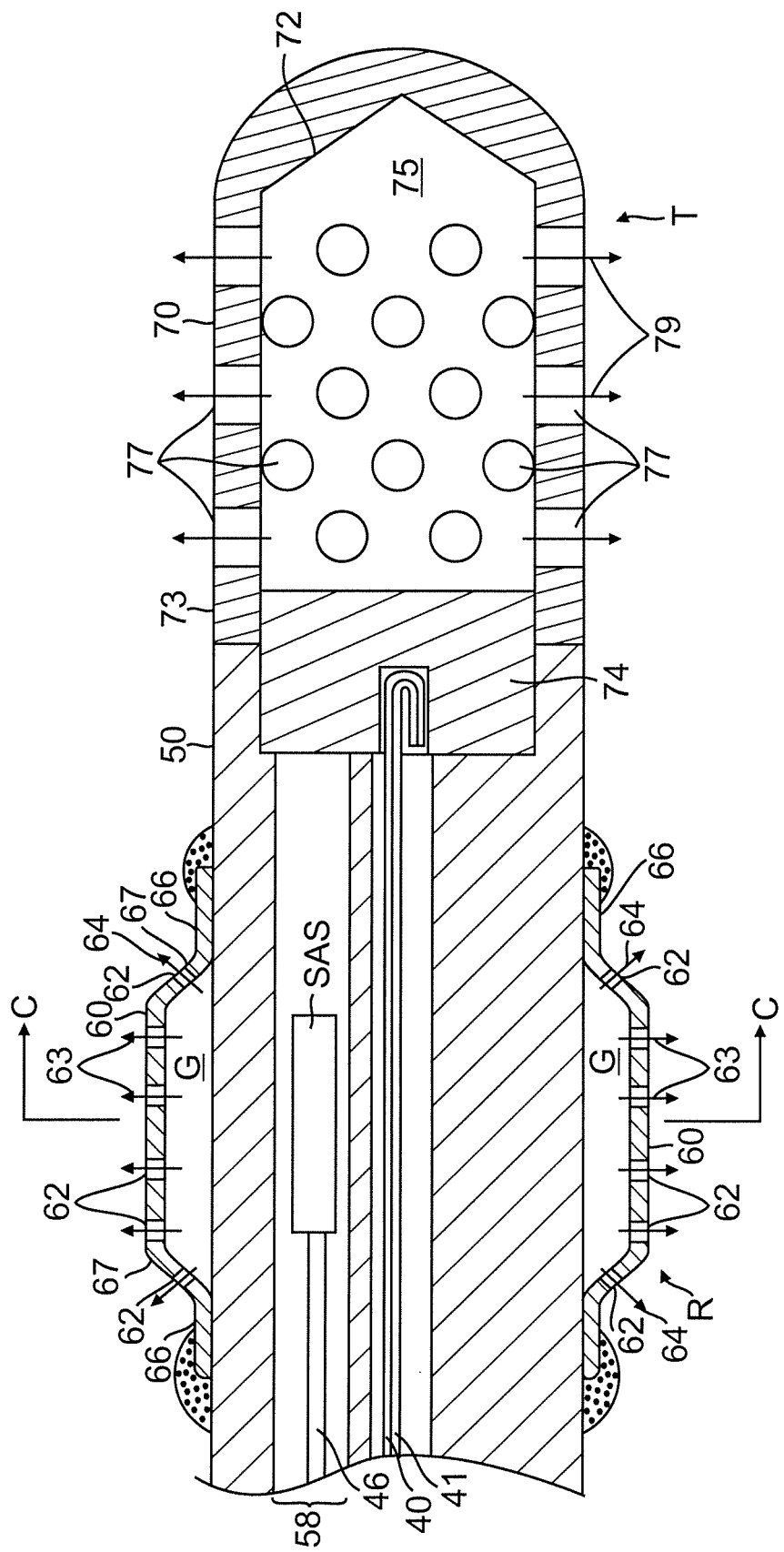
FIG. 6A is a partial side cross-sectional view of the distal section of FIG. 5 taken generally along a diameter.
Figure 6B:
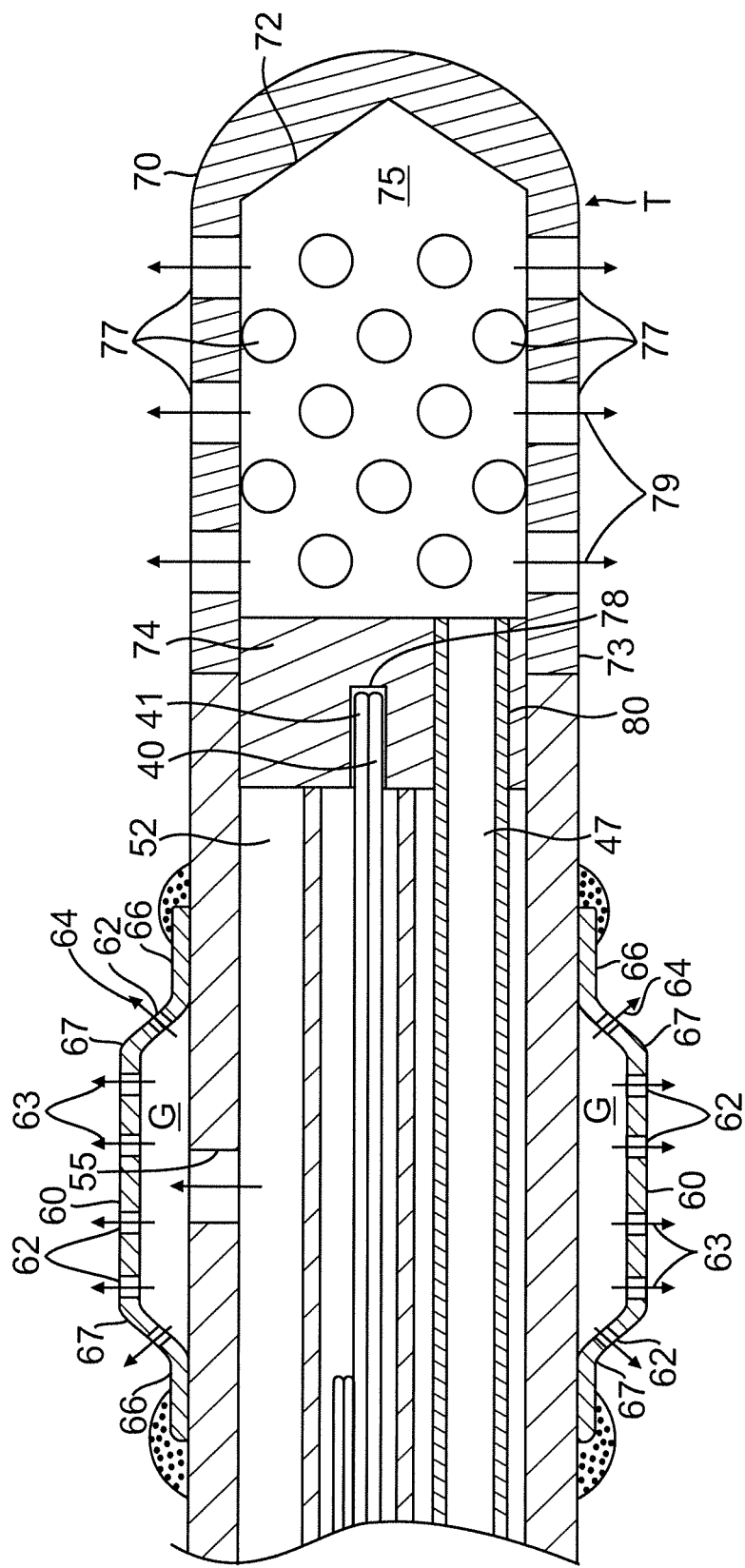
FIG. 6B is a partial side cross-sectional view of the distal section of FIG. 5, taken generally along another diameter.
Figure 6C:
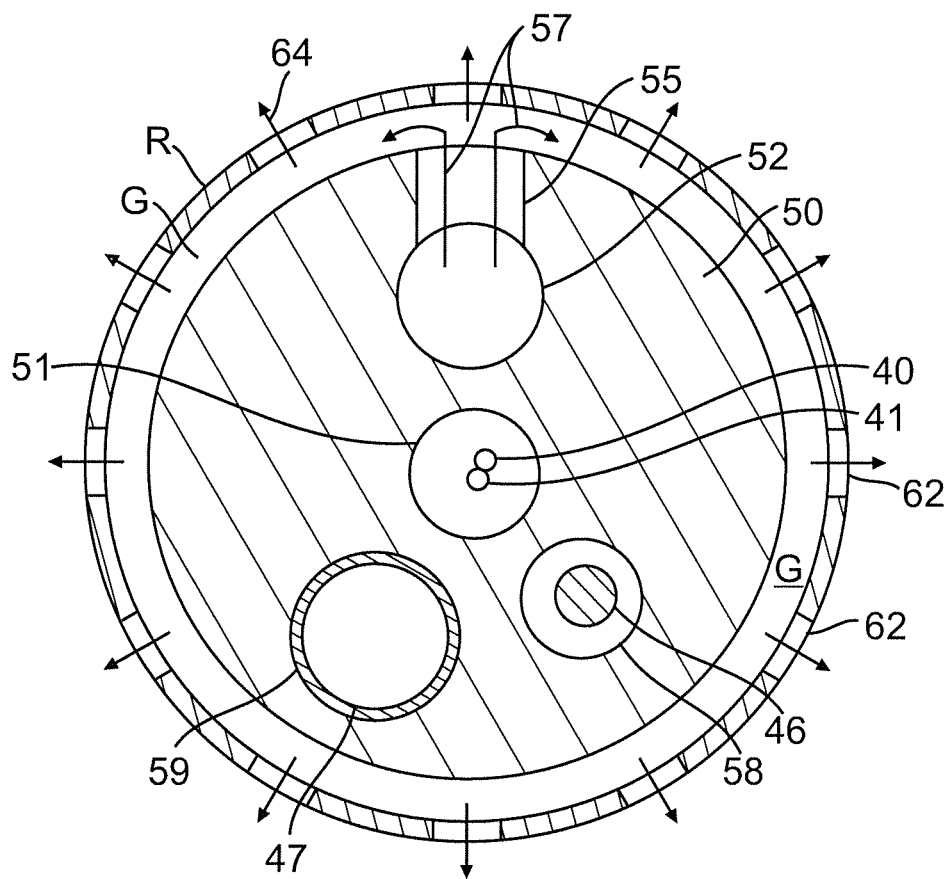
FIG. 6C is an end cross-sectional view of the distal section of FIG. 5, taken along line C-C.
Figure 7:
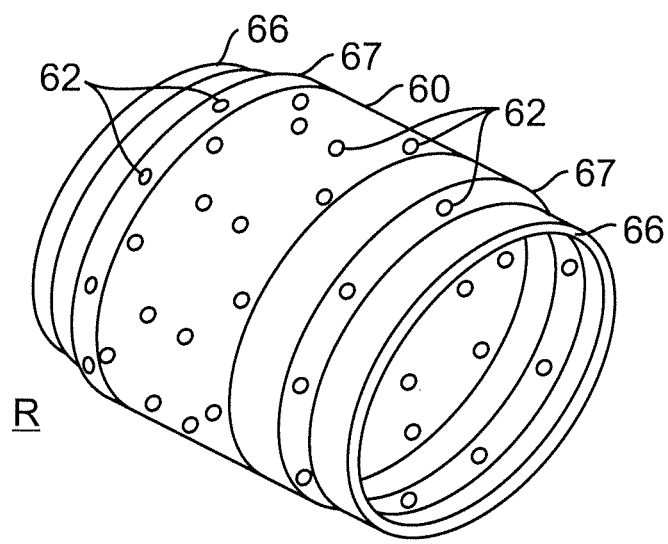
FIG. 7 is an embodiment of an irrigated ring electrode.

With reference to FIGS. 6A, 6B, the ring electrode R is adapted for ablation and irrigation. The ring electrode is generally cylindrical with a length greater than its diameter. The ring electrode has a side cross-section that can resemble a barrel with a side wall 60 that bulges radially between opposing end portions 66. Curved transitional regions 67 are provided between the side wall 60 and the end portions 66 to provide an atraumatic profile without corners or sharp edges.

With reference to FIG. 6C, a reservoir or annular gap G exists around the exterior of the tubing 50 of the distal section 17. The gap G provides improved fluid distribution from the second lumen 52 to the exterior of the ring electrode via apertures 62. The size of the opening 55 in the tubing 50 varies with the position along the length of the distal section 17. For optimum flow, the more distal an opening 55 is along the distal section 17, the greater the size or cross-section of the opening and/or the plurality of openings 55 under each ring electrode.

The apertures 62 are arranged the side wall 60 in a predetermined pattern including axially offset rows. These apertures face outwardly promoting flow in a radial direction (see arrows 63). Apertures are also provided in or near the curved transitional regions 67 to promote flow more in an axial direction (see arrows 64). Moreover, these apertures are particularly effective in minimizing charring and coagulation at or near the curved transitional regions 67 which are likely to be "hot spots" resulting from higher current densities due to transitions in the electrode profile. In that regard, the plurality and/or cross-section of the apertures 62 is greater at or near the curved transitional regions 67 than in the side wall 60 of the electrode so as to provide more cooling in the curved transitional regions. Other suitable ring electrodes are described in US Patent Application Publication No. US2010/0168548 A1, and U.S. patent application Ser. No. 13/174,742, filed Jun. 30, 2011, the entire content of both of which are hereby incorporated by reference.

The tip electrode T on a distal end of the tubing 50 of the distal section 17 has a shell 70 having a U-shaped cross section defining an interior cavity 72 with an open proximal end 73 that is sealed by a plug 74 to form a plenum chamber 75 in the tip electrode. A plurality of irrigation apertures 77 are formed in radial wall of the shell to allow fluid which collects in the plenum chamber to exit to outside of the tip electrode (see arrows 79).

An axial passage 80 formed in the plug 73 receives one of the irrigation tubing. In the illustrated embodiment, the second irrigation tubing 47 extends through the passage 80 and terminates at or near a distal face of the plug 74 so that fluid passing through the tubing 47 feeds into the plenum chamber 75. The plug 74 is sized to form a fluid tight seal at the open end 73. The plug 74 also has a blind hole 78 formed on the proximal face to receive a lead wire/thermocouple pair 40, 41 for electrical communication with the tip electrode. To that end, both the plug 74 and shell 70 are made of electrically-conductive material so that electrical energy can pass between the lead wires and the shell. Like the ring electrodes, the tip electrode can be made of any suitable noble metal, such as platinum or gold, preferably a combination of platinum and iridium or gold and platinum.

In accordance with a feature of the present invention, the catheter 10 is adapted to provide separate and dedicated irrigation flow pathways to different electrodes or different sets of electrodes. The selection and division among electrodes can be made on the bases of position of an electrode (e.g., distal or proximal) and/or its type or function (e.g., tip/ring, uni-polar/bi-polar, or focal/connecting). In the disclosed embodiment, the division among electrodes is made between the distal tip electrode and all proximal ring electrodes, such that a first flow pathway is dedicated to supplying the tip electrode to the exclusion of the ring electrodes, and a second flow pathway is dedicated to supplying all the ring electrodes to the exclusion of the tip electrode. For example, the first irrigation tubing 43 supplies fluid solely to all of the ring electrodes and the second irrigation tubing 47 supplies fluid solely to the tip electrode.

It is understood by one of ordinary skill in the art that the division may also be made based solely on position among a distal section of a catheter that carries a plurality of electrodes of an identical type or function. For example, on a distal section with ring electrodes only, a first flow pathway can be dedicated to supplying a proximal portion of the ring electrodes, and a second flow pathway can be dedicated to supplying a distal portion of the ring electrodes.

With reference to FIGS. 2, 4A and 4B, in the disclosed embodiment, irrigation fluid is delivered to the ring electrodes by the first irrigation tubing 43 whose distal end terminates in the second lumen 52 of the tubing 50 of the distal section 17 a relatively short distance distal of a proximal end of the tubing 50. The first irrigation tubing 43 extends proximally through the second lumen 34 of the tubing 15 of the intermediate section 14, the central lumen 18 of the catheter body 12, and the control handle 16. The proximal end of the tubing 43 is attached to a first luer hub 80a which is connected to a first pump tubing 81a whose proximal end is attached to a first drip chamber 83a that is in turn attached to a first fluid source FS1. A first pump head PH1 acts on a portion of the tubing 81a extending between the first luer hub 80a and the fluid source FS1.

Irrigation fluid is delivered to the tip electrode by the second irrigation tubing 47 which extends through the blind hole 80 of the tip electrode plug 74, the fourth lumen 59 of the tubing 50 of the distal section 17, the fifth lumen 37 of the tubing 15 of the intermediate section 14, the central lumen 18 of the catheter body 12, and the control handle. The proximal end of the tubing 47 is attached to a second luer hub 80b which is connected to a second pump tubing 81*b* whose proximal end is attached to a second drip chamber 83*b* that is in turn attached to a second fluid source FS2. A second pump head PH2 acts on a portion of the tubing 81*b* extending between the second luer hub 80*b* and the fluid source FS2.

Figure 8A:
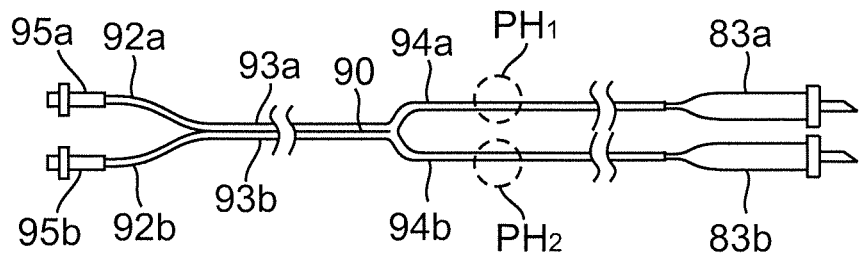
FIG. 8A is top plan view of one embodiment of an irrigation tubing set in accordance with the present invention.
Figure 8B:
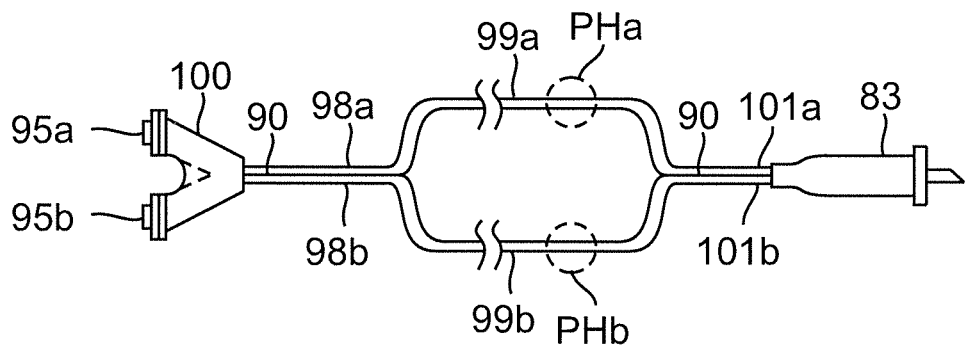
FIG. 8B is a top plan view of another embodiment of an irrigation tubing set in accordance with the present invention.

Suitable embodiments of pump tubing sets with a plurality of elongated pump tubings providing parallel flow for connection between the fluid sources FSi and control handle 16 are illustrated in FIGS. 8A and 8B. For various portions of the tubing set, the respective tubings are either bonded and joined along a common longitudinal seam 90, or are separated and detached from each other.

The embodiment of FIG. 8A includes a plurality of luer fittings 95*a*, 95*b* adapted to fit and connect with the luer hubs 80, a distal portion of unjoined tubings 92*a*, 92*b*, a mid-portion of joined tubings 93*a*, 93*b*, a proximal portion of unjoined tubings 94*a*, 94*b* each adapted for engagement with a respective one of pump heads PH1, PH2 of the same plurality, and drip chambers 83*a*, 83*b* of the same plurality adapted for fluid communication with respective fluid sources of the same plurality.

The embodiment of FIG. 8B includes a manifold 100 with a plurality of termination devices or luer fittings 95*a*, 95*b*, a distal portion of joined tubings 98*a*, 98*b*, a mid-portion of unjoined tubings 99*a*, 99*b*, each adapted for engagement with a respective one of pump heads PH1, PH2 of the same plurality, and a proximal portion of joined tubings 101*a*, 101*b*, each of which is connected to a common drip chamber 83 adapted for fluid communication with a fluid source. The length of the tubing sets is not critical, nor the length of each portion, so long as the length(s) are sufficient to allow appropriate access to the pump heads and manipulation of the catheter. It is understood that the plurality of pump tubings, luer fittings, drip chambers, etc. can vary depending on the number and types of electrodes carried on the catheter.

Figure 9A:
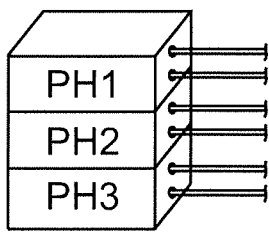
FIGS. 9A-9C are schematic representations of different embodiments of an irrigation pump with multiple pump heads in accordance with the present invention.
Figure 9C:
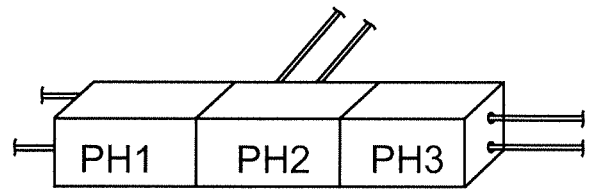
Figure 9B:
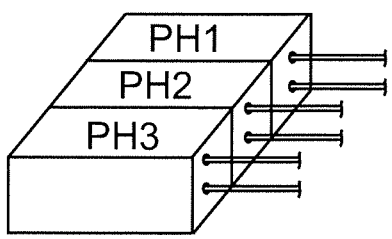

It is also understood that the number of pump heads PH of the irrigation pump 27 can also vary as appropriate or needed. The pump heads can be oriented and arranged is any appropriate manner on the irrigation pump. For example, the pump heads (of any plurality) can be stacked vertically (FIG. 9A), side-by-side (FIG. 9B), end-to-end (FIG. 9C), or combinations thereof.

The proximal end of each electrode lead wire is electrically connected to a suitable connector at the distal end of the control handle 16 for connection to the RF generator 11. A pair of wires 40, 41 is provided for each electrode. In the disclosed embodiment, wire 40 of the wire pair is a copper wire, e.g. a number "40" copper wire and the wire 41 is a constantan wire. The wires of each pair are electrically isolated from each other except at their distal ends where they are twisted together. Attachment to the respective ring electrode R is accomplished by feeding the wire pair through a hole formed in the side wall into the first lumen 51 of the tubing 50 of the distal section 17, and soldering to the respective ring electrode (see FIG. 6B). The wire pairs for each electrode (ring and tip) extend distally from the control handle 16, through the central lumen 18 of the catheter body 12, the first lumen 33 of the intermediate section 14, and the first lumen 51 of the distal section 17. RF energy, is delivered to the electrodes via the wire 40 of the wire pairs. However, as understood by one of ordinary skill in the art, the wire pairs inclusive of their respective constantan wire can also function as temperature sensors or thermocouples sensing temperature of each electrode.

All of the wire pairs pass through a common nonconductive protective sheath 42 (FIG. 4C), which can be made of any suitable material, e.g., polyimide, in surrounding relationship therewith. The sheath 42 extends from the control handle 16, the catheter body 12, the intermediate section 14, and terminates just distal of the proximal end of the distal section 17. The distal end is anchored in the first lumen 51 by glue, for example, polyurethane glue or the like.

The pair of deflection puller wire 44*a*, 44*b* are provided for deflection of the intermediate shaft 14. The puller wires 44*a*, 44*b* extend through the central lumen 18 of the catheter body 12 and each through a respective one of the third and sixth lumens 35 and 38 of the intermediate section 14. They are anchored at their proximal ends in the control handle 16, and at their distal end to a location at or near the distal end of the intermediate section 14 by means of T-bars 102 (FIG. 4C) that are affixed to the sidewall of the tubing 15 by suitable material 103, e.g., polyurethane, as generally described in U.S. Pat. No. 6,371,955, the entire disclosure of which is incorporated herein by reference. The puller wires are made of any suitable metal, such as stainless steel or Nitinol, and is preferably coated with Teflon® or the like. The coating imparts lubricity to the puller wire. For example, each puller wire has a diameter ranging from about 0.006 to about 0.010 inch.

As seen in FIGS. 4A and 4B, each puller wire has a respective compression coil 105 in surrounding relation thereto. Each compression coil 105 extends from the proximal end of the catheter body 12 to at or near the proximal end of the intermediate section 14 to enable deflection. The compression coils are made of any suitable metal, preferably stainless steel, and are each tightly wound on itself to provide flexibility, i.e., bending, but to resist compression. The inner diameter of the compression coils is preferably slightly larger than the diameter of a puller wire. The Teflon® coating on the puller wire allows it to slide freely within the compression coil. Within the catheter body 12, the outer surface of the compression coil is covered by a flexible, non-conductive sheath 106, e.g., made of polyimide tubing. The compression coils are anchored at their proximal ends to the outer wall 30 of the catheter body 12 by proximal glue joints and to the intermediate section 14 by distal glue joints.

Within the third and sixth lumens 35, 38 of the intermediate section 14, the puller wires 44*a*, 44*b* extend through a plastic, preferably Teflon®, puller wire sheath 107 (FIG. 4B), which prevents the puller wires from cutting into the wall of the tubing 15 of the intermediate section 14 when the intermediate section 14 is deflected.

Longitudinal movement of the puller wires 44*a*. 44*b* relative to the catheter body 12 for bi-directional deflection is accomplished by appropriate manipulation of the control handle 16. A deflection knob 110 (FIG. 1) is provided on the handle which can be pivoted in a clockwise or counterclockwise direction for deflection in the same direction. Suitable control handles for manipulating more than one wire are described, for example, in U.S. Pat. Nos. 6,468,260, 6,500, 167, and 6,522,933 and U.S. application Ser. No. 12/960, 286, filed Dec. 3, 2010, the entire disclosures of which are incorporated herein by reference.

In one embodiment, the position sensor 48 includes a plurality of single axis sensors ("SAS") carried on the cable 46 that extends through the third lumen 46 of the distal section 17 (FIG. 4C), where each SAS occupies a known or predetermined position along the length of the distal section. The cable 46 extends proximally from the distal section 17 through the fourth lumen 36 of the intermediate section 14 (FIG. 6), the central lumen 18 of the catheter body 12, and into the control handle 16. Each SAS can be positioned with a known and equal spacing separating adjacent SASs. In the disclosed embodiment, the cable carries three SASs that are positioned under the distal-most ring electrode (FIG. 6A), the proximal-most ring electrode, and a mid ring electrode, for sensing location and/or position of the distal section. The SASs enable the distal section to be viewed under mapping systems manufactured and sold by Biosense Webster, Inc., including the CARTO, CARTO XP and NOGA mapping systems. Suitable SASs are described in U.S. application Ser. No. 12/982,765, filed Dec. 30, 2010, the entire disclosure of which is incorporated herein by reference.

Figure 10:
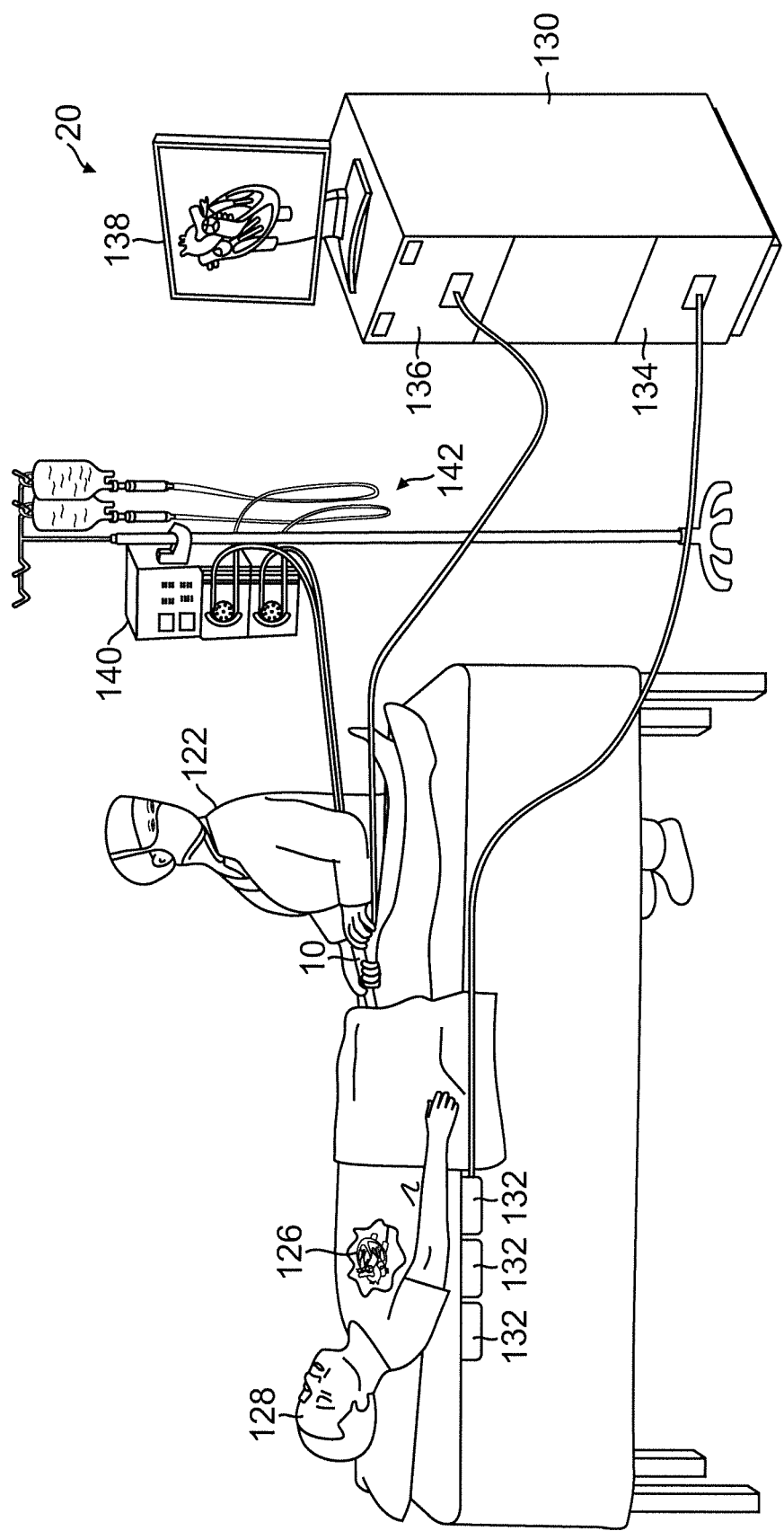
FIG. 10. is a schematic pictorial illustration of a system for ablation of tissue in the heart, in accordance with an embodiment of the present invention.

FIG. 10 is a schematic pictorial illustration of a system S for ablation of tissue in a heart 126 of a patient 128, in accordance with an embodiment of the present invention. An operator 122, such as a cardiologist, inserts a catheter 10 through the vascular system of the patient so that the distal end of the catheter enters a chamber of the patient's heart. Operator advances the catheter so that the distal section 17 of the catheter engages endocardial tissue at a desired location or locations, as shown in FIG. 5. Catheter 10 is connected by a suitable connector at its proximal end to a console 130. The console comprises an RF generator 136 for applying RF energy through tip and ring electrodes on the distal section of the catheter in order to ablate the tissue contacted by the distal section.

Responsive to signals from the RF generator 136 representing the energization states of each electrode on the catheter, an irrigation pump 140 with multiple pump heads is adapted to provide irrigation fluid to the catheter at at least two different flow rates. The irrigation pump is used with a pump tubing set 142 that defines at least two separate fluid flow pathways for at least two separate irrigation tubings in the catheter. As such, selected electrodes or sets of electrodes supplied by the separate irrigation tubings can have fluid flowing through at different rates, and preferably in accordance with the energization states of the electrodes. FIG. 11 is a table of sample flow rates for different operating conditions.

In the pictured embodiment, system S uses magnetic positioning sensing to determine position coordinates of the distal assembly of the catheter inside heart. To determine the position coordinates, a driver circuit 134 in console 130 drives field generators 132 to generate magnetic fields within the body of patient. Typically, field generators comprise coils, which are placed below the patient's torso at known positions external to the body. These coils generate magnetic fields in a predetermined working volume that contains heart. One or more magnetic field sensors, such as the SASs, within the distal section of the catheter generate electrical signals in response to these magnetic fields. The console 130 processes these signals in order to determine the position (location and/or orientation) coordinates of the distal section 17 of the catheter. Console may use the coordinates in driving a display 138 to show the location and status of the catheter. This method of position sensing and processing is described in detail, for example, in PCT International Publication WO 96/05768, whose entire disclosure is incorporated herein by reference, and is implemented in the CARTO system produced by Biosense Webster Inc. (Diamond Bar, Calif.).

The operator may first pass a sheath percutaneously through the vascular system and into the heart through the ascending vena cava. The catheter is then inserted through the sheath until the distal section 17 of the catheter extends past the distal end of the sheath and is exposed for contact with the target tissue in the heart. The operator may rotate the control handle and/or use the deflection knob 110 of the control handle 16 to maneuver catheter in directing the distal section 17 toward the target tissue. The operator may carry out this alignment using the position sensing methods described above, along with a pre-acquired map or image of heart as displayed on the display 138. Alternatively or additionally, the alignment may be performed under fluoroscopic or other means of visualization.

With reference to FIG. 5, the catheter 10 is well adapted to form linear or continuous lesions, such as a "roof line" in the left atrium. For example, when the tip electrode T and ring electrodes R1-RN of the distal section 17 are positioned in contact with the target tissue, the tip electrode T and ring electrodes R are energized (with the latter energized as uni-polar electrodes) to ablate and form a plurality of focal lesions 110 (solid lines). Being in communication with and responsive to the RF generator, the irrigation pump activates the motor controls of both pump heads to supply the tip and ring electrodes with fluid at rates suitable for cooling, for example, the "Linear Ablation" rates of FIG. 12.

While the catheter 10 remains in the same position, the ring electrodes R can then be energized as bi-polar electrodes to ablate and form connecting lesions 112 (broken lines) between the focal lesions 110 thus forming a generally linear or continuous lesion. With the tip electrode de-energized or inactivated, the irrigation pump signals the motor control of the pump head that supplies fluid to the tip electrode to decrease flow, for example, to lower the flow rate from "Linear Ablation" rate to "Maintenance Flow" rate, while continuing to activate the pump head supplying fluid to the ring electrodes at "Linear Ablation" rate. Because the catheter need not be repositioned, ablation procedure time is reduced and clinical efficacy is improved.

If touch up of broken or incomplete lesion lines is desired, the catheter can be repositioned such that the tip electrode T forms additional focal lesions to complete the linear or continuous lesion. With only the tip electrode energized, the irrigation pump signals the motor control of the pump head for the tip electrode to provide flow at "Focal Ablation" while signaling the motor control of the pump head for the ring electrodes to provide flow at "Maintenance Flow."

Although FIG. 10 shows a particular system configuration, other system configurations may be used in alternative embodiments of the present invention. For example, the methods described hereinbelow may be applied using position transducers of other types, such as impedance-based or ultrasonic position sensors. The term "position transducer" as used herein refers to an element mounted on or in catheter that causes console to receive signals indicative of the coordinates of the element. The position transducer may thus comprise a received in the catheter, which generates a position signal to the control unit based on energy received by the transducer; or it may comprise a transmitter, emitting energy that is sensed by a receiver external to the probe. Furthermore, the methods described hereinbelow may similarly be applied in mapping and measurement applications using not only catheters, but also probes of other types, both in the heart and in other body organs and regions.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. Any feature or structure disclosed in one embodiment may be incorporated in lieu of or in addition to other features of any other embodiments, as needed or appropriate. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter comprising:
   an elongated body;
   a distal section having a tubing, a tip electrode at a distal end of the tubing, and at least one ring electrode electrically isolated on the distal section from the tip electrode, the tip electrode having a plurality of tip electrode irrigation apertures and the at least one ring electrode comprising a plurality of ring electrode irrigation apertures in a sidewall of the ring electrode, the plurality of tip electrode irrigation apertures being the only irrigation apertures in the tip electrode, and the plurality of ring electrode irrigation apertures being the only irrigation apertures in the at least one ring electrode;
   a control handle proximal the elongated body;
   a first irrigation tubing configured to transport fluid within the catheter to all of the tip electrode irrigation apertures without transporting fluid within the catheter to the ring electrode irrigation apertures; and
   a second irrigation tubing configured to transport fluid within the catheter to all of the ring electrode irrigation apertures without transporting fluid within the catheter to the tip electrode irrigation apertures, wherein the first irrigation tubing and the second irrigation tubing are isolated from each other in the distal section.

2. A catheter of claim 1, wherein the at least one ring electrode comprises at least two ring electrodes, and the second irrigation tubing is configured to transport fluid within the catheter to all of the ring electrode apertures of each of the at least two ring electrodes without transporting fluid within the catheter to the tip electrode irrigation apertures.

3. A catheter of claim 1, wherein each of the first and second irrigation tubings extends between the distal section and the control handle.

4. A catheter of claim 1, wherein the tip electrode and the at least one ring electrode are adapted for uni-polar ablation.

5. A catheter of claim 1, wherein the tip electrode and the at least one ring electrode are adapted for bi-polar ablation.

6. A catheter of claim 1, wherein each of the at least one ring electrodes is adapted for uni-polar and bi-polar ablation.

7. A catheter of claim 1, further comprising an electrically conductive plug inside the distal section, the electrically conductive plug overlapping a joint between the tip electrode and the tubing.

8. A catheter comprising:
   an elongated body;
   a distal section having a tubing, a tip electrode at a distal end of the tubing, and a plurality of ring electrodes electrically isolated on the distal section from the tip electrode and proximal of the tip electrode, the tip electrode having a plurality of tip electrode irrigation apertures and each of the plurality of ring electrodes comprising a plurality of ring electrode irrigation apertures, the plurality of tip electrode irrigation apertures being the only irrigation apertures in the tip electrode, and the plurality of ring electrode irrigation apertures being the only irrigation apertures in each of the plurality of ring electrodes;
   a control handle proximal the elongated body;
   a first irrigation tubing configured to transport fluid within the catheter to all of the tip electrode irrigation apertures without transporting fluid within the catheter to the ring electrode irrigation apertures; and
   a second irrigation tubing configured to transport fluid within the catheter to all of the ring electrode apertures of the plurality of ring electrodes without transporting fluid within the catheter to the tip electrode, wherein the first irrigation tubing and the second irrigation tubing are isolated from each other in the distal section.

9. A catheter of claim 8, wherein the plurality of ring electrodes comprises at least five ring electrodes, and the second irrigation tubing is configured to transport fluid within the catheter to all the ring electrode irrigation apertures of each of the at least five ring electrodes without transporting fluid within the catheter to the tip electrode irrigation apertures.

* * * * *